United States Patent [19]

Seguchi

[11] Patent Number: 4,473,702

[45] Date of Patent: Sep. 25, 1984

[54] METHOD FOR PRODUCING DIALLYL ESTER OF AROMATIC DICARBOXYLIC ACID

[75] Inventor: Koji Seguchi, Ibaraki, Japan

[73] Assignee: Kureha Kagaku Kogyo Kabushiki Kaisha, Tokyo, Japan

[21] Appl. No.: 477,843

[22] Filed: Mar. 22, 1983

Related U.S. Application Data

[63] Continuation-in-part of Ser. No. 204,358, Nov. 5, 1980, abandoned.

[30] Foreign Application Priority Data

Nov. 15, 1979 [JP] Japan ............................ 54-147026

[51] Int. Cl.$^3$ ............................................. C07C 67/03
[52] U.S. Cl. ...................................... 560/80; 560/95; 560/99; 502/154
[58] Field of Search ............................ 560/95, 99, 80; 252/429 C, 431 R, 442, 461, 463, 472, 431 C

[56] References Cited

U.S. PATENT DOCUMENTS

| | | | |
|---|---|---|---|
| 2,491,660 | 12/1949 | Gresham | 560/99 |
| 3,332,983 | 7/1967 | Barie et al. | 560/95 X |
| 3,341,570 | 9/1967 | Barie | 560/99 |
| 3,784,578 | 1/1974 | Swodenk et al. | 560/99 |

FOREIGN PATENT DOCUMENTS

| | | |
|---|---|---|
| 1211625 | 3/1966 | Fed. Rep. of Germany . |
| 49-38259 | 10/1974 | Japan . |
| 810381 | 3/1959 | United Kingdom . |
| 999947 | 7/1965 | United Kingdom . |
| 1038285 | 8/1966 | United Kingdom . |
| 1136688 | 12/1968 | United Kingdom . |

*Primary Examiner*—Natalie Trousof
*Assistant Examiner*—Vera C. Clarke
*Attorney, Agent, or Firm*—Wegner & Bretschneider

[57] ABSTRACT

A novel method for producing a diallyl ester of an aromatic dicarboxylic acid, particularly a diallyl ester of an aromatic symmetrical dicarboxylic acid by ester-exchange of a dialkyl ester of the aromatic dicarboxylic acid with allyl alcohol in the co-presence of two kinds of catalysts is disclosed.

The obtained diallyl ester of an aromatic dicarboxylic acid according to the present invention is excellent in transmissivity.

5 Claims, 5 Drawing Figures

METHOD FOR PRODUCING DIALLYL ESTER OF AROMATIC DICARBOXYLIC ACID

CROSS-REFERENCE TO RELATED APPLICATION

This invention is a continuation-in-part of U.S. Pat. application Ser. No. 204,358 filed Nov. 5, 1980, now abandoned.

SUMMARY OF THE INVENTION

In an aspect of the invention, there is provided a method for producing a diallyl ester of an aromatic dicarboxylic acid, comprising heating an ester of an aromatic dicarboxylic acid and allyl alcohol at a temperature of 100° to 200° C. in the presence of a mixture consisting essentially of one part by mole of catalyst (A) and 0.01 to 5 parts by mole of catalyst (B), the catalyst (A) being at least one organic tin compound of the formula (I):

where $R^1$ and $R^2$ respectively represent an alkyl group of 1 to 8 carbon atoms or a phenyl group, and X represents two halogen atoms or an oxygen atom and the amount of the organic tin compound being 0.3 to 5 mole % of the ester of the aromatic dicarboxylic acid, the catalyst (B) being at least a simple substance of or a compound of a metallic element selected from the group consisting of magnesium, zinc, tin, lead, aluminum, nickel and zirconium.

BACKGROUND AND DETAILED DESCRIPTION OF THE INVENTION

The present invention relates to a method for producing diallyl ester of an aromatic dicarboxylic acid having an excellent transmissivity by ester-exchange reaction between dialkyl ester of the aromatic dicarboxylic acid and allyl alcohol, particularly a novel method for obtaining diallyl esters of a symmetrical aromatic dicarboxylic acid at a high yield.

Polymerization product of diallyl ester of a symmetrical aromatic dicarboxylic acid, for instance, that of diallyl terephthalic acid, is excellent in electric properties, dimensional stability, heat resistance, weatherproofness, resistance to chemicals and mechanical properties as compared to the polymerization product of diallyl ester of non-symmetrical aromatic dicarboxylic acid and accordingly, the former has been broadly utilized as electrical material, mechanical material and construction material. Further, recently, it has been found that the above-mentioned polymer is also excellent in optical properties such as transparency, refractive index and surface hardness, and the polymer is expected as optical material.

As the conventional method for producing diallyl ester of aromatic dicarboxylic acid, the following methods have been known:

(1) a method of directly esterifying aromatic dicarboxylic acid with allyl alcohol, (2) a method of condensing metal salt of aromatic dicarboxylic acid with allyl halide in the presence of tertiary amine as a catalyst in an aqueous medium or in an anhydrous reaction system, and (3) a method of ester-exchange reaction between ester of aromatic dicarboxylic acid and allyl alcohol.

However, the method of direct esterification (1) proceeds slowly and so it is necessary to carry out the reaction at a high temperature for a long time period accompanied by unfavorable phenomena such as polymerization of allyl alcohol and colouring of the reaction product. Moreover, the reactivity of symmetrical aromatic dicarboxylic acid and allyl alcohol in the direct reaction is unfavorably poor.

The method for producing diallyl ester of aromatic dicarboxylic acid according to (2), that is, by condensation of them, has been and is now most generally adopted, however, the method has its demerits as follows: in the case where the reaction is to be carried out in an anhydrous system, its necessitates troublesome processes such as condensing and drying the metal salt of aromatic dicarboxylic acid prepared in an aqueous solution. In addition, in the case where the reaction is carried out in an aqueous medium, by-products derived from hydrolysis of allyl halide are apt to be formed, and accordingly, there are problems of separation of by-products and purification of the main product. Moreover, the metal salt of symmetrical aromatic dicarboxylic acid which is used as a starting material for producing allyl ester of the symmetrical aromatic dicarboxylic acid is hard to be synthesized and accordingly, the method has not yet been adopted on industrial base.

On the other hand, the method (3), that is, by ester-exchange, has attracted the attention of those skilled in the art as a method for which the starting materials are easily available and which can be carried out under mild reaction conditions. However, the use of a catalyst in the above-mentioned ester-exchange reaction is indispensable, and it is no exaggeration to say that the industrial values such as the productivity, cost, etc. are mainly determined by the result of selection of the catalyst. Hitherto, as a catalyst for use in the above-mentioned reaction, sodium methoxide, metallic magnesium, tetrabutyl titanate, organic tin compounds, etc. have been known. According to the results of tracing experiment on the above-mentioned method by the inventor of the present invention, the above-enumerated catalysts have demerits in the ester-exchange reaction (with ester of symmetrical aromatic dicarboxylic acid and allyl alcohol) such as their lower catalystic activity not to give a high yield and the tendencies of formation of by-products, polymers and colouration. So, it is an important problem to develop a catalyst for use in producing diallyl ester of aromatic dicarboxylic acid, particularly of symmetrical aromatic dicarboxylic acid, of high in activity and effective in suppressing the side-reactions such as polymerization.

The inventor of the present invention, after having studied the above-mentioned problem, has found that a specific catalyst specifically accelerates the reaction of ester-exchange between ester of aromatic dicarboxylic acid and allyl alcohol while suppressing the side-reactions such as polymerization and addition, thus giving the intended product at a high yield, and has attained the present invention.

It is an object of the present invention to provide a method for producing a diallyl ester of an aromatic dicaboxylic acid, comprising heating an ester of an aromatic dicarboxylic acid and allyl alcohol at a temperature of 100° to 200° C. in the presence of a mixture consisting essentially of one part by mole of catalyst(A) and 0.01 to 5 parts by mole of catalyst(B), the catalyst(A) being at least one organic tin compound of the formula (I):

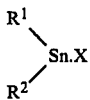

where $R^1$ and $R^2$ respectively represent an alkyl group of 1 to 8 carbon atoms or a phenyl group, and X represents two halogen atoms or an oxygen atom and the amount of the organic tin compound being 0.3 to 5 mole % of the ester of the aromatic dicarboxylic acid, the catalyst(B) being at least a simple substance of or a compound of a metallic element selected from the group consisting of magnesium, zinc, tin, lead, aluminum, nickel and zirconium.

In the drawing:

FIG. 1 shows the composition of the reaction mixture with the time passage in Example 1 (Curves A-1, A-2 and A-3) and Comparative Examples 3 (Curves B-1, B-2 and B-3).

A-1 shows the relationship between the amount of starting material and the time of reaction; A-2 shows the relationship between the amount of diallyl terephthalate and the time of reaction; and A-3 shows the relationship between the amount of allyl methyl terephthalate and the time of reaction in Example1.

B-1, B-2 and B-3 respectively show the same relationship in/comparative Example 3 as in A-1, A-2 and A-2 in Example 1e 1.

C-1, C-2 and C-3 respectively show the same relationship in Example 4 as in A-1, A-2 and A-3 in Example 1.

D-1, D-2 and D-3 in Comparative Example 6 show the same relationship as in Example 1.

Figure 4:
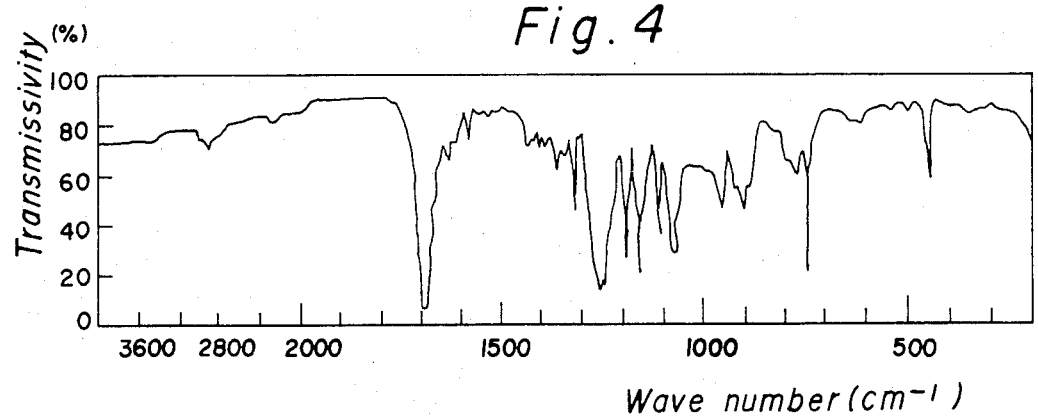

FIG. 4 shows an infrared absorption spectrogram of diallyl 2,6-naphthalenedicarboxylate obtained in Example 6.

Figure 5:
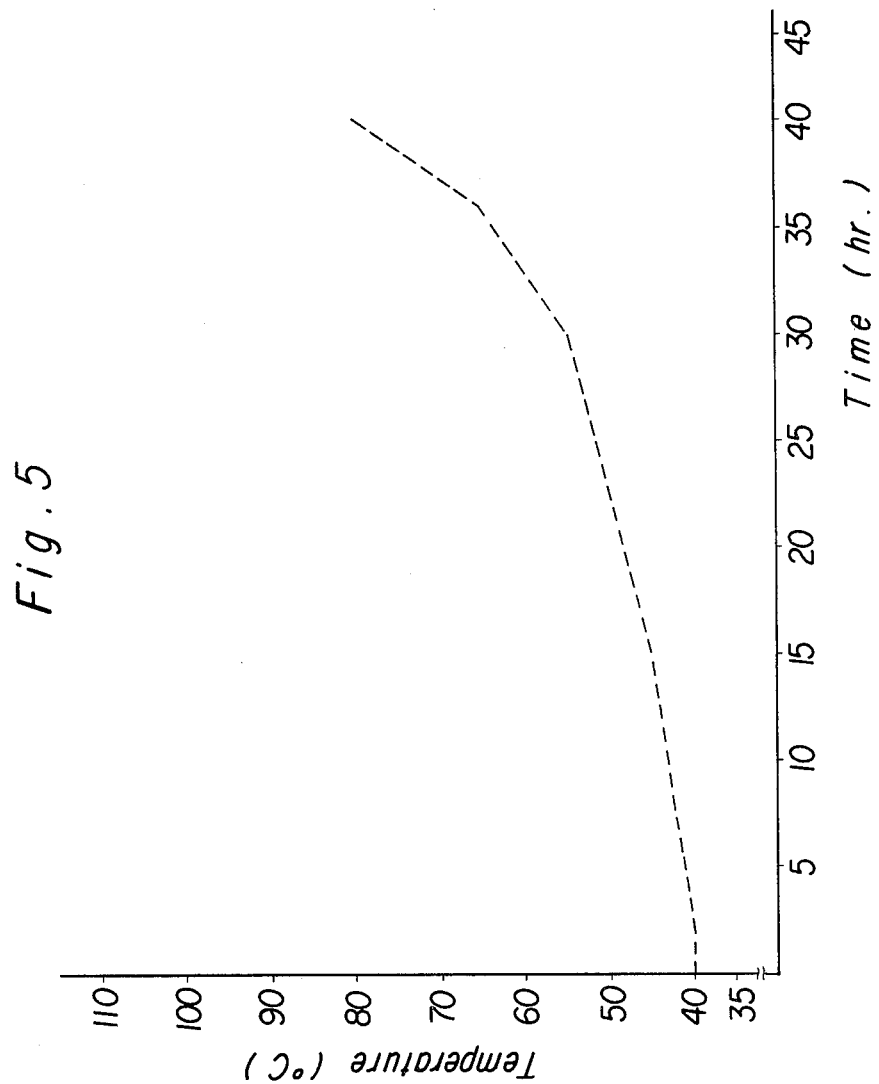

FIG. 5 shows a graph showing the relation between a reaction temperature and a reaction time on the polymerization of diallyl terephtalate in Examples 1 and 2.

The followings are the more detailed description of the present invention.

The ester of an aromatic dicarboxylic acid for use in the present invention is represented by the general formula (II):

wherein $R^3$ and $R^4$ represent the same or different alkyl of 1 to 3 carbon atoms, and Ar represents one group selected from the groups consisting of phenylene, naphthylene, biphenylene, anthrylene, phenanthrylene and acenaphthenylene, and concretely, the acidic component of the ester of aromatic dicarboxylic acid includes phthalic acid, isophthalic acid, terephthalic acid, 2,6-naphthalenedicarboxylic acid, 2,7-naphthalenedicarboxylic acid, 1,5-naphthalenedicarboxylic acid, biphenyldicarboxylic acids, anthracenedicarboxylic acids, acenaphthenedicarboxylic acid, and the like. On the other hand, the alcoholic component of the above-mentioned ester includes methanol, ethanol, propanol and isopropyl alcohol.

The ester of an aromatic dicarboxylic acid of the present invention comprising the above-mentioned acidic component and the above-mentioned alcoholic component is used singly or as a mixture of more than two species of the esters. In addition, the acidic component of the esters of the symmetrical aromatic dicarboxylic acid includes terephthalic acid, 2,6-naphthalenedicarboxylic acid, 4,4'-biphenyldicarboxylic acid, and 9,10-, 1,5- or 2,6- anthracenedicarboxylic acid and the like.

The organic tin compound represented by the formula (I) for use in the present invention as a catalyst (hereinafter referred to as Catalyst(A)) is, for instance, dimethyltin dichloride, diethyltin dichloride, dibutyltin dichloride, dimethyltin dibromide, dibutyltin dibromide, dioctyltin dichloride, diphenyltin dichloride, dimethyltin oxide, diethyltin oxide, dibutyltin oxide, dioctylin oxide, diphenyltin oxide and the like. A single compound or a mixture of more than two of the above-mentioned compounds is used in the present invention.

On the other hand, another catalyst (hereinafter referred to as Catalyst(B)) for use in the present invention together with Catalyst (A) includes the following single substance or a mixture of the substances: metallic magnesium, magnesium methoxide, zinc dust, zinc oxide, metallic tin, tin oxide, lead acetate, aluminum oxide, nickel oxide, aluminum ethoxide, zirconium acetate, and the like.

The production of a diallyl ester of an aromatic dicatboxylic acid according to the method of the present invention is very simply carried out. That is, more than two mols of allyl alcohol and one mol of the above-mentioned ester of an aromatic dicarboxylic acid are mixed and the mixture is heated in the co-presence of Catalyst A and Catalyst B at a temperature of 100° to 200° C., preferably of 110° to 150° C. for 1 to 25 hours, preferably for 3 to 20 hours to bring them into reaction. The molar ratio of allyl alcohol to the ester is theoretically 2, however, in order to accelerate the reaction and to use allyl alcohol also as a solvent, the actual molar ratio is made to 2.5 to 15 in the charge, preferably.

In addition, the inventor of the present invention has found that also in the case where methallyl alcohol is used instead of allyl alcohol in the above-mentioned ester-exchange reaction in the co-presence of Catalyst (A) and Catalyst (B), di-methallyl ester of an aromatic dicarboxylic acid is readily obtainable at a high yield in a relatively short time of reaction.

The amount of Catalyst (A) used in the reaction is 0.3 to 5 mol %, preferably 0.5 to 3 mol % to the ester of aromatic dicarboxylic acid because of the smaller effectiveness at less than 0.3 mol %, and of no more improvement of the effectiveness at more than 5 mol %.

The amount of Catalyst (B) used in the reaction is 0.01 to 5 parts by mol per one part by mole of Catalyst (A), preferably 0.1 to 2 parts by mol, the reason of selecting the above-mentioned range being the same as in the case of Catalyst (A). However, in the case where Catalyst (B) does not dissolve in allyl alcohol in the reaction system, the amount should be a little more, say, 0.5 to 2 parts by mol per one part by mole of Catalyst (A).

The reaction is usually carried out under a normal pressure and reflux-condensing of allyl alcohol, however, in order to improve the reaction efficiency, the system is vigorously agitated or a method is adopted in which the formed alcohol is distilled out of the system as soon as formed and additional charge of allyl alcohol is carried out continuously, at least one rectifying column being provided to the reactor as a means for that purpose of distilling the thus formed alcohol.

After the reaction is over, the products are separated from the reaction mixture by distillation or recrystallization. In the case where the main product is liquid, it is purified by distillation under reduced pressure from the reaction mixture, and on the other hand, in the case where the main product separates as crystals as in the case of diallyl 2,6-naphthalate, re-crystallization is carried out to isolate and purify the product while using an organic solvent.

As has been stated, diallyl ester of an aromatic dicarboxylic acid is obtainable according to the present invention within a very short time period at a high yield resulting in a large contribution to industry.

The present invention is explained more in detail while referring to the non-limitative examples as follows:

EXAMPLE 1

Production of diallyl terephthalate

Into a three-necked flask provided with two rectifying columns on the two necks, 77.6 g of dimethyl terephthalate, 92.8 g of allyl alcohol, 1.21 g of dibutyltin dichloride and 0.13 g of zinc dust were introduced, and the content was heated at 130° C. using an oil bath. The distillation of methanol from the flask through the rectifying column continued for 5 hours amounting to the distilled methanol of 31.9 ml. Gas-chromatographical data showed that the reaction mixture at the time of ending of the distillation of methanol was consisted of 99.5% by weight of the object-product, diallyl terephthalate, and of the rest, 0.5% by weight, of a by-product, allyl methyl terephthalate. No other impurities were detected by gas-chromatography.

Figure 1:
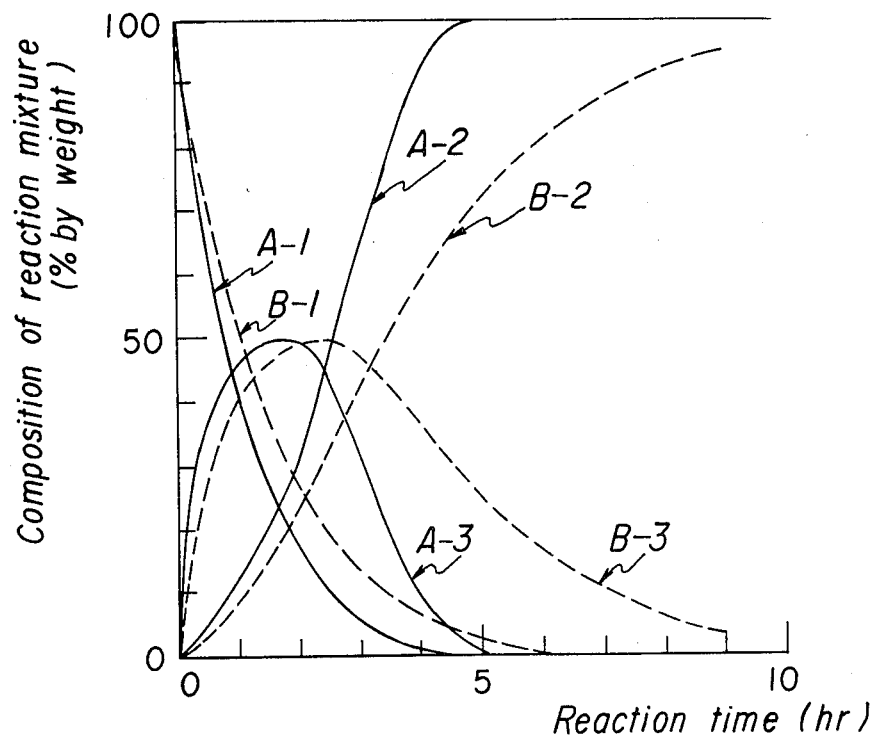

During the above-mentioned reaction, sampling of the reaction mixture was carried out every one hour from the starting of heating, and the sampled specimens were directly subjected to examination by gas-chromatography to determine the respective amounts of unreacted ester, produced diallyl terephthalate and by-produced allyl methyl terephthalate versus the time of heating. The results of the determination are shown in FIG. 1 by Curve A with the conditions of gas-chromatography of a rate of temperature rise of 10° C./min and at a temperature range of 100° to 250° C. while using a Model SE-30 gas chromatographic apparatus made by Gasukuro Industry Co. Japan.

After the reaction was over, an excess of allyl alcohol in the flask was removed by heating under reduced pressure, and the remaining crude product in the flask was separated from zinc dust by filtration as a filtrate, and directly distilled under reduced pressure of 5 mmHg while collecting the fraction distilling at a boiling point of 162° to 164° C. The fraction amounted to 96.1 g.

Figure 2:
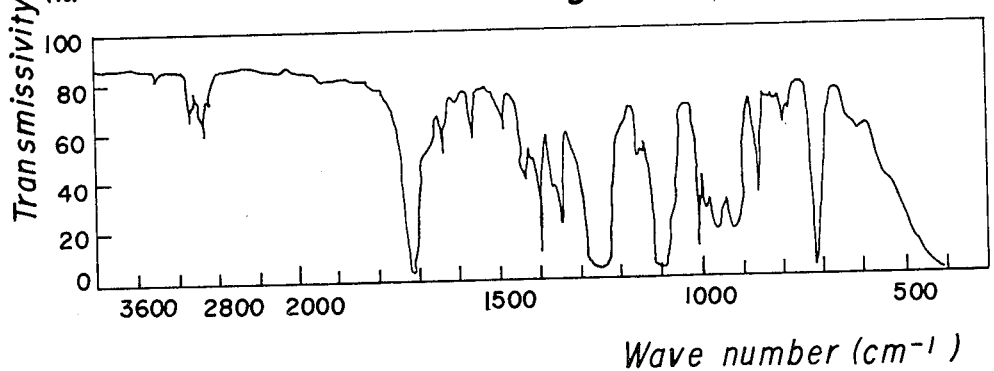
FIG. 2 shows aninfrared absorption spectrogram of the diallyl terephthalate obtained in Example 1.

The thus obtained product was a clear and colourless liquid of specific gravity of 1.119, of reflective index of $n_D^{20°}$ of 1.5283, of a viscosity at 24° C. of 15 cP. The elementary analytical data, the gas-chromatographic analytical data and infrared absorption spectrum of the compound were coincided with those of the authentic specimen of diallyl terephthalate. FIG. 2 shows an infrared absorption spectrum diallyl terephthalate obtained in Example 1 according to the present invention.

The transmissivity of the thus obtained diallyl terephthalate to a light wave of 450 nm measured by photoelectric spectrophotometer (model EPS-3T, made by Hitachi Ltd.) was 99%.

A mixture of 10 g of the thus obtained diallyl terephthalate and 0.3 g of diisopropyl peroxydicarbonate as a polymerization initiator was heated under gaseous nitrogen from 40° to 80° C. during 40 hours with the time course of its temperature shown by a dotted curve in FIG. 5 to obtain a polymer. The transmissivity of the thus obtained polymer at 450 nm was 92.5%.

COMPARATIVE EXAMPLE 1

Production of diallyl terephthalate

A mixture of 77.6 g of dimethyl terephthalate, 92.8 g of allyl alcohol and 1.51 g of dibutyltin dichloride was heated as in Example 1, and after 10 hour-heating, the reaction mixture was subject directly to gas-chromatography to find that the reaction mixture was composed of 54.1% by weight of diallyl terephthalate, 19.3% by weight of allyl methyl terephthalate and 26.6% by weight of unreacted substances.

COMPARATIVE EXAMPLE 2

Production of diallyl terephthalate

A mixture of 77.6 g of dimethyl terephthalate, 92.8 g of allyl alcohol and 0.26 g of zinc dust was heated as in Example 1 for 10 hours. Then, the reaction mixture was directly subjected to gas-chromatography to find that the reaction mixture was composed of 15.1% by weight of diallyl terephthalate, 53.5% by weight of allyl methyl terephthalate and the balance of unreacted substances.

COMPARATIVE EXAMPLE 3

Production of diallyl terephthalate

A mixture of 79.6 g of dimethyl terephthalate, 92.8 g of allyl alcohol, 1.21 g of dibutyltin dichloride and 0.22 g of sodium methylate was heated for 9 hours as in Example 1, and then, the reaction mixture was examined directly by gas-chromatography to find that the reaction mixture was composed of 95.3% by weight of diallyl terephthalate, 4.5% by weight of allyl methyl terephthalate and the balance of unreacted substances. The amount of recovered methanol was 31.3 ml.

As in Example 1, sampling of the reaction mixture and gas-chromatography examination of the component of the samples were carried out every one hour from the commencement of heating, and the results of the examination were shown in FIG. 1 by Curve B.

As are clearly seen in Example 1 and Comparative Examples 1 to 3, it was necessary to carry out the reaction for longer time period in the cases where the organic tin compound or metal was singly used as in Comparative Examples 1 and 2, than in the case where the reaction was carried out in the co-presence of Catalysts (A) and (B) as in Example 1, and the rate of reaction was slower in the case where a metal other than those of the present invention was used.

EXAMPLE 2

A mixture of 38.8 g of diethyl terephthalate, 46.4 g of allyl alcohol, 1.21 g of dibutyltin dichloride and 0.32 g of zinc oxide was heated for 4.5 hours at 130° C. as in Example 1, and then, the reaction mixture was directly subjected to gas-chromatography to find out that the reaction mixture was composed of 98.5% by weight of diallyl terephthalate and 1.5% by weight of allyl ethyl terephthalate.

After filtering the reaction mixture for the removal of zinc oxide and partly undissolved dibutyltin dichloride, the filtrate was directly distilled under a reduced pressure of 5 mmHg. The fraction distilling at 162 to 164 under the pressure was 47.1 g.

The infrared absorption spectrum, the elementary analytical data, the specific gravity and the refractive index of the thus obtained fraction coincided with those of authentic diallyl terephthalate.

The transmissivity of the thus obtained diallyl terephthalate to a light wave of 450 nm measured by a photoelectric spectrophotometer (model EPS-3T, made by Hitachi Ltd.) was 99%.

A mixture of 10 g of the thus obtained diallyl terephthalate and 0.3 g of diisopropyl peroxydicarbonate as a polymerization initiator was heated under gaseous nitrogen from 40° to 80° C. during 40 hours with the time course of its temperature shown by a dotted curve in FIG. 5 to obtain a polymer. The transmissivity of the thus obtained polymer at 450 nm was 93%.

COMPARATIVE EXAMPLE 4

A mixture of 38.8 g of diethyl terephthalate, 46.4 g of allyl alcohol, 1.36 g of diphenyltin dichloride and 0.34 g of tetrabutyl titanate was heated for 4.5 hours at 130° C. as in Example 1, and then, the reaction mixture was directly subjected to gas-chromatography to find out that the reaction mixture was composed of 99.7% by weight of allyl ethyl terephthalate.

After filtering the reaction mixture for the removal of tetrabutyl titanate and partly undissolved diphenyltin dichloride, the filtrate was directly distilled under a reduced pressure of 5 mmHg. The fraction distilling distilling at 162° to 164° C. under the pressure was 46.1 g.

The infrared absorption spectrum, the elementary analytical data, the specific gravity and the refractive index of the thus obtained fraction coincided with those of authentic diallyl terephthalate.

The transmissivity of the thus obtained fraction measured by the same technique as in Example 2 was 95%, and the transmissivity of the polymer obtained by polymerizing the fraction with the same technique as in Example 2 was 85%.

COMPARATIVE EXAMPLE 5

A mixture of 77.6 g of dimethyl terephthalate, 92.8 g of allyl alcohol and 0.325 g of zinc oxide was heated as in Example 1 for 10 hours. Then, the reaction mixture was directly subjected to gas-chromatography to find that the reaction mixture was composed of 21.5% by weight of diallyl terephthalate, 52.8% by weight of allyl methyl terephthalate.

EXAMPLE 3

A mixture of 88.8 g of diethyl terephthalate, 98.6 g of allyl alcohol, 1.21 g of dibutyltin dichloride and 0.32 g of zinc oxide was heated as in Example 1 at 130° C. for 5 hours, and the reaction mixture was directly subjected go gas-chromatography to find that the reaction mixture was composed of 98.1% by weight of diallyl terephthalate and 1.9% of allyl ethyl terephthalate.

After filtering the reaction mixture to removed zinc oxide and partly undissolved dibutyltin dichloride, the filtrate was directly distilled under reduce pressure of 5 mmHg. The fraction distilling at 162° to 164° C. at the pressure was 95.1 g. The infrared absorption spectrum, the elementary analytical data, the specific gravity and the reflactive index of the thus obtained product coincided with those of authentic diallyl terephthalate.

EXAMPLE 4

Figure 3:
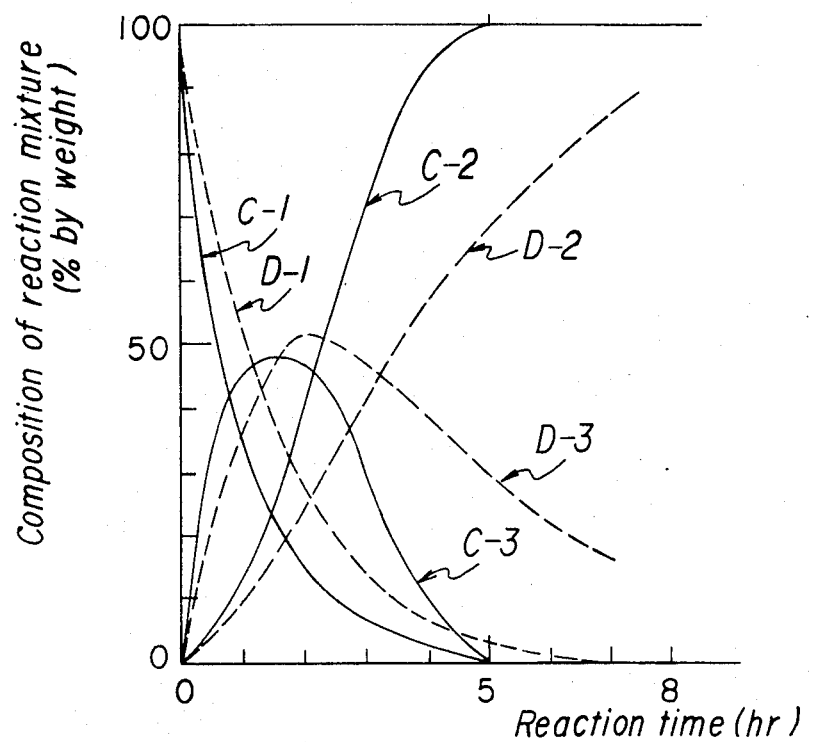
FIG. 3 shows the composition of the reaction mixture with the time passage in Example 4 (C-1, C-2 and C-3) and in Comparative Example 6 (D-1, D-2, and D-3).

A mixture of 77.6 g of dimethyl terephthalate, 98.6 g of allyl alcohol, 0.99 g of dibutyltin oxide and 0.46 g of tin oxide was heated as in Example 1 at 130° C. for 5 hours, and sampling was carried out every one hour from the commencement heating, the samples being subjected directly to gas-chromatography to obtain the information on the reaction and to show the information by Curve C in FIG. 3. After the 5 hour heating, the reaction mixture was distilled as in Example 1 to collect 95.2 g of a colourless and transparent liquid at 162° to 164° C./5 mmHg. The product was identified as diallyl terephthalate from the coincidence of its infrared spectrum, its elementary analytical sample of diallyl terephthalate.

COMPARATIVE EXAMPLE 6

A mixture of 77.6 g of dimethyl terephthalate, 98.6 g of allyl alcohol, 1.23 g of dibutyltin oxide was heated as in Example 4 at 130° C., and during the heating, sampling of the reaction mixture was carried out every one hour. The samples were directly subjected to gas-chromatography to obtain the information on the composition of the reaction mixture with the passage of time. The information is shown in FIG. 3 by Curves D. As is seen in FIG. 3, in the present case of using only one kind of catalysts; that is Catalyst (A), the rate of reaction was smaller than that in Example 4, and it took a longer period to complete the reaction than in Example 4.

EXAMPLE 5

A mixture of 77.6 g of dimethyl terephthalate, 69.6 g of allyl alcohol, 0.92 g of dibutyltin dichloride, 0.99 g of dibutyltin oxide and 0.096 g of metallic magnesium was heated as Example 1 at 130° C. for 5 hours. The distillation of methanol stopped after 5 hour-heating with the amount of 32.1 ml. The gas-chromatography information on the reaction mixture was 99.7% by weight of diallyl terephthalate and 0.3% by weight of allyl methyl terephthalate, impurities being not observed.

On distilling the reaction mixture directly under reduced pressure of 5 mmHg, the fraction distilling at 162° to 164° C. was collected in an amount of 96.5 g. The thus obtained colourless and transparent liquid showed an infrared absorption spectrum, elementary analytical data and other properties coinciding with those of the authentic sample of diallyl terephthalate.

Example 6

Production of diallyl 2,6-naphthalenedicarboxylate

A mixture of 24.2 g of dimethyl 2,6-naphthalenedicarboxylate, 58.0 g of allyl alcohol, 0.91 g of dibutyltin dichloride, and 0.26 g of magnesium methoxide was, in the same manner as in Example 1, heated at 130° C. After heating for 15 hours, distillation of methanol was over, the amount of distilled methanol being 6.7 ml. The result of direct chromatography of the reaction product showed the composition of 99.5% by weight of diallyl 2,6-naphthalenedicarboxylate and 0.5% by weight of allyl methyl 2,6-naphthalenedicarboxylate, the other substance being not detected.

After removing excess allyl alcohol by distillation under reduced pressure, the crude product was dissolved into methanol while heating, and after removing the insoluble substance by filtration, the filtrate was cooled to obtain white needlelike crystals in an amount of 23.5 g. By comparing the data of infrared absorption spectrum, of elementary analysis and of nuclear magnetic resonance spectrum with those of the authentic sample, the product was identified as diallyl 2,6-naphthalenedicarboxylate. Infrared absorption spectrum of the product is shown in FIG. 4.

Elementary analysis, found: 73.0% of C and 5.4% of H, calcd. as $C_{18}H_{16}O_4$: 72.97% of C and 5.4% of H.

The transmissivity of the thus obtained fraction measured by the same technique as in Example 2 was 99%, and the transmissivity of the polymer obtained by polymerizing the fraction with the same technique as in Example 2 was 93%.

EXAMPLES 7 to 10

Five runs of production of diallyl terephthalate were respectively carried out by heating 38.8 g of dimethyl terephthalate, 46.4 g of allyl alcohol with each one of the organic tin compounds and each of the metals or metal compounds shown in Table 1 of each amounts thereof also shown in Table 1, in the same manner as in Example 1. When the reaction was over, the reaction mixture was subjected to distillation under reduced pressure as in Example 1. The fraction distilling at 162° to 164° C./5 mmHg was collected to be examined by infrared absorption spectroscopy and elementary analysis. All the products in the four runs were identified as diallyl terephthalate.

The amount of diallyl terephthalate in the reaction mixture and the yield of distilled diallyl terephthalate of each run is shown also in Table 1.

catalyst (A) and 0.01 to 5 parts by mole of catalyst(B), said catalyst (A) being at least one organic tin compound of the formula (I):

where $R^1$ and $R^2$ respectively represent an alkyl group of 1 to 8 carbon atoms or a phenyl group, and X represents two halogen atoms or an oxygen atom and the amount of said organic tin compound being 0.3 to 5 mol % of said ester of the aromatic dicarboxylic acid, said catalyst(B) being at least a simple substance of or a compound of a metallic element selected from the group consisting of magnesium, zinc, tin, lead, aluminum, nickel and zirconium.

2. The method according to claim 1, wherein the ester of aromatic dicarboxylic acid is a compound of the formula

wherein Ar is phenylene, naphthylene, biphenylene, anthrylene, phenanthrylene or acenaphthenylene, and $R^3$ and $R^4$ represent the same or different alkyl of 1 to 3 carbon atoms.

3. The method according to claim 1 or 2, wherein the ester of aromatic dicarboxylic acid is a symmetric compound.

4. The method according to claim 1, wherein the organic tin compound is selected from the group consisting of dimethyltin dichloride, diethyltin dichloride, dibutyltin dichloride, dimethyltin dibromide, dibutyltin dibromide, dioctyltin dichloride, diphenyltin dichloride, dimethyltin oxide, diethyltin oxide, dibutyltin oxide, dioctyltin oxide and diphenyltin oxide.

5. The method according to claim 1, wherein the

TABLE 1

Conditions of synthesis of diallyl terephthalate and Results of Synthesis

| Example | Organic tin compound | | Metal or its compound | | Reaction time (hour) | Amount of the ester[2] (g) | Yield of the ester[1] (%) |
|---|---|---|---|---|---|---|---|
| | Name | amount (g) | Name | amount (g) | | | |
| 7 | $(Octyl)_2SnCl_2$ | 2.48 | Magnesium | 0.048 | 5.0 | 46.3 | 99.5 |
| 8 | $(Methyl)_2SnO$ | 0.65 | $Al_2O_3$ | 0.20 | 5.0 | 44.5 | 98.6 |
| 9 | $(Phenyl)_2SnO$ | 0.86 | $(CH_3COO)_2Pb$ | 0.44 | 5.5 | 46.0 | 99.1 |
| 10 | $(Octyl)_2SnO$ | 1.44 | NiO | 0.14 | 6.0 | 43.6 | 96.5 |

Notes:
[1] Yield of diallyl terephthalate in the reaction mixture, respresented % by weight.
[2] Amount of pure diallyl terephthalate distilling at 162 to 164° C./5 mmHg.

What is claimed is:

1. A method for producing a diallyl ester of an aromatic dicarboxylic acid, comprising heating an ester of an aromatic dicarboxylic acid and allyl alcohol at a temperature of 100° to 200° C. in the presence of a mixture consisting essentially of one part by mole of simple substance or the compound of the element is metallic magnesium, zinc dust, metallic tin, magnesium methoxide, zinc oxide, tin oxide, lead acetate, aluminum oxide, nickel oxide, aluminum ethoxide or zirconium acetate.

* * * * *